United States Patent [19]
Blumen et al.

[11] Patent Number: 5,459,031
[45] Date of Patent: Oct. 17, 1995

[54] METHODS FOR CONTROLLING SIALIC ACID DERIVATIVES IN RECOMBINANT GLYCOPROTEINS

[75] Inventors: Tracy K. Blumen; Gustavo E. Grampp; David J. Hettwer, all of Thousand Oaks, Calif.

[73] Assignee: Amgen Inc., Thousand Oaks, Calif.

[21] Appl. No.: 261,697

[22] Filed: Jun. 17, 1994

Related U.S. Application Data

[63] Continuation of Ser. No. 148,298, Nov. 5, 1993, abandoned.

[51] Int. Cl.$^6$ .............................. C12Q 3/00; C12Q 1/00; C12N 5/00; C12P 21/00
[52] U.S. Cl. .................. 435/3; 435/4; 435/7.21; 435/69.4; 435/70.1; 435/70.3; 435/240.2
[58] Field of Search ................... 435/3, 4, 7.21, 435/70.1, 70.3, 240.2, 284, 69.4

[56] References Cited

U.S. PATENT DOCUMENTS

| | | | |
|---|---|---|---|
| 4,703,008 | 10/1987 | Lin | 435/204.2 |
| 4,954,437 | 9/1990 | Beck et al. | 435/240.2 |
| 5,272,070 | 12/1993 | Lehrman et al. | 435/240.2 |

FOREIGN PATENT DOCUMENTS 9105795  5/1991  WIPO .

OTHER PUBLICATIONS

Derwent Abs. 87–353301/50 Otsuka Pharm KK (J62258324) Nov. 10, 1987.
Biotech Abs. 93–05618 "Appl. Microbiol. Biotech" (1993) vol. 38, #4, pp. 458–462 von Hunolstein et al.
Schauer, R., *Biochemical Society Transactions*, 11:270–271 (1983).
Schauer, R., *Glycobiology*, 1:449–452 (1991).
Hokke et al, *FEBS*, 275:9–14 (1990).
Tsao et al., *Annals N.Y. Academy Science*, 665:127–136 (1992).
Goochee, C. and Monica, T., *Biotechnology*, 8:421–427 (1990).
Derwent Abstract 87–151423 Otsuka Pharm KK J62258324 (Nov. 10, 1987).

*Primary Examiner*—Herbert J. Lilling
*Attorney, Agent, or Firm*—Stuart L. Watt; Craig A. Crandall

[57] ABSTRACT

The invention relates to the effects of certain cell culture and/or production parameters on the carbohydrate composition of a cell culture-derived recombinant glycoprotein. The methods of the invention demonstrate a practical method for controlling levels of a sialic acid derivative, NGNA, in secreted recombinant glycoproteins which will be useful in a variety of bioprocessing systems.

22 Claims, 8 Drawing Sheets

METHODS FOR CONTROLLING SIALIC ACID DERIVATIVES IN RECOMBINANT GLYCOPROTEINS

This is a continuation of application Ser. No. 08/148,298 filed Nov. 5, 1993 which is hereby incorporated by reference now abandoned.

BACKGROUND OF THE INVENTION

The present invention relates to a process for producing a recombinant glycoprotein wherein certain cell culture and/or production parameters are monitored and adjusted so as to control sialylation of the recombinant glycoprotein. In particular, the invention is to a process comprising a method wherein the level of $CO_2$ is monitored and adjusted thereby controlling N-glycolylneuraminic acid (NGNA) levels in the oligosaccharide groups of the recombinant glycoprotein.

Most cell surface and secretory proteins produced by eucaryotic cells are modified with one or more oligosaccharide groups. This modification, referred to as glycosylation, occurs at specific locations along the polypeptide backbone and is usually of two types: O-linked oligosaccharides are attached to serine or threonine residues while N-linked oligosaccharides are attached to asparagine residues when they are part of the sequence Asn-X-Ser/Thr, where X can be any amino acid except proline. Glycosylation can dramatically affect the physical properties of proteins and can also be important in protein stability, secretion, and subcellular localization. Proper glycosylation can be essential for biological activity. In fact, some genes from eucaryotic organisms, when expressed in bacteria (e.g., *E. coli*) which lack cellular processes for glycosylating proteins, yield proteins that are recovered with little or no activity by virtue of their lack of glycosylation.

The structures of N-linked and O-linked oligosaccharides and the sugar residues found in each type are different. One type of sugar that is commonly found on both N-linked and O-linked oligosaccharides is sialic acid. Sialic acid is a generic name for a group of about 30 naturally occurring acidic carbohydrates that are essential components of a large number of glycoconjugates. Schauer, *Biochem. Society Transactions*, 11, 270–271 (1983). Sialic acids are usually the terminal residue of the oligosaccharides. Sialylation of recombinant glycoproteins is very important and may impart many significant properties to the glycoprotein including the following: (1) charge; (2) antigenicity; (3) resistance to protease attack; (4) immunogenicity; (5) plasma clearance rate; and (6) bioactivity.

N-acetylneuraminic acid (NANA) is the most common sialic acid form and N-glycolylneuraminic acid (NGNA) is the second most common form. Schauer, *Glycobiology*, 1, 449–452 (1991). NGNA differs from NANA by the presence of a hydroxyl group on the acetyl moiety, and formally results from the enzymatic hydroxylation of the sugar nucleotide CMP-NANA to form CMP-NGNA, followed by transfer of NGNA from the CMP-NGNA to the glycoprotein by a sialytransferase. Alternatively, NGNA can be produced by the biosynthetic pathway for NANA by replacing N-acetylmannosamine (a component of NANA biosynthesis) with N-glycoloylmannosamine. N-glycoloylmannosamine is derived as a natural breakdown product of NGNA.

NGNA is widespread throughout the animal kingdom and, according to species and tissue, often constitutes a significant proportion of the glycoconjugate-bound sialic acid. Certain species such as chicken and man are exceptional, since they lack NGNA in normal tissues. Corfield, et al., *Cell Biology Monographs*, 10, 5–50 (1982). In human serum samples, the percentage of sialic acid in the form of NGNA is reported to be 0.01% of the total sialic acid. Schauer, "Sialic Acids as Antigenic Determinants of Complex Carbohydrates", found in *The Molecular Immunology of Complex Carbohydrates*, (Plenum Press, New York, 1988). NGNA has been described as an oncofetal antigen since it has been reported in fetal tissue and is found on the cell surface membrane coat of some tumor cells. Hirabayashi, et al., *Japan Journal of Cancer Research*, 78, 251–260 (1987).

Recombinant glycoproteins produced in mammalian cell lines like Chinese hamster ovary (CHO) cells have been found to contain NGNA as a minor form of sialic acid. Hokke, et al., FEBS, 275, 9–14 (1990). To date, there have been no reports of antibodies to NGNA on these recombinant glycoproteins. The ability to limit or control levels of NGNA in recombinant glycoproteins could be useful to those evaluating recombinant glycoproteins for therapeutic use.

A glycoprotein capable of production in eucaryotic cells is erythropoietin (EPO). Erythropoietin is a glycoprotein hormone produced in CHO cells and involved in the maturation of erythroid progenitor cells into erythrocytes. It is essential in regulating levels of red blood cells in circulation. Naturally occurring erythropoietin is produced by the liver during fetal life and by the kidney of adults and circulates in the blood and stimulates the production of red blood cells in bone marrow. Anemia is almost invariably a consequence of renal failure due to decreased production of erythropoietin from the kidney. Recombinant erythropoietin produced by genetic engineering techniques involving the expression of a protein product from a host cell transformed with the gene encoding erythropoietin has been found to be effective when used in the treatment of anemia resulting from chronic renal failure.

Recombinant erythropoietin derived from CHO cells has the amino acid sequence 1–165 of human erythropoietin and contain three N-linked and one O-linked oligosaccharide chains which together comprise about 40% of the total molecular weight of the glycoprotein. N-linked glycosylation occurs at asparagine residues located at positions 24, 38 and 83 while O-linked glycosylation occurs at a serine residue located at position 126 (Lai et al. J. Biol. Chem. 261, 3116 (1986); Broudy et al. Arch. Blochem. Biophys. 265, 329 (1988)).

The process of glycosylation and the factors which affect it are not well understood. Of the factors known to influence the structures of protein-bound oligosaccharides, cell metabolism is the most difficult to control. In a study reported by Tsao, E., et al. in *Annals New York Academy of Sciences*, 665: 127–136 (1992), the effects of various process parameters, including growth and production kinetics, incubation temperature, rotation rate, $CO_2$ gassing, inoculum density, and inoculum generation number, on both the growth of the recombinant CHO cells and the production of EPO in roller bottles, were characterized. The studies allowed Tsao, et al. to optimize a roller bottle process, and better deal with various process disturbances.

There have been several reports relating to effects of cell culture parameters on carbohydrate structure in general. For example, N-linked glycosylation was shown to be influenced by cell culture variables such as glucose concentration, ammonium ion concentration and the hormonal content of the medium. Goochee et al., *Biotechnology*, 8: 421–427

(1990). In addition, it has been reported that the heterogeneity of glycoprotein oligosaccharides could be influenced by endogenous CHO cell sialidase released into the extracellular medium. Gramer et al., *Biotechnology Prog.*, 4:366–373 (1993).

However, nothing can be drawn from the literature regarding the effect of various cell culture and/or production parameters on the NGNA composition of a cell culture-derived recombinant glycoprotein. This invention demonstrates that the monitoring and adjusting of one such parameter, e.g., $CO_2$, during biosynthesis can help control the NGNA composition of a secreted recombinant glycoprotein. This is very important to those working in the field because it demonstrates that process changes, even those considered benign, can lead to significant product glycosylation changes.

SUMMARY OF THE INVENTION

The present invention is directed to a process for the production of recombinant glycoproteins wherein certain cell culture and/or production parameters are monitored and adjusted thereby controlling the carbohydrate composition of the glycoprotein. In particular, the invention is directed to a process wherein liquid phase $pCO_2$ is monitored and adjusted so as to control the NGNA levels present in the carbohydrate moiety of the glycoprotein. Surprisingly, the relative and/or absolute amount of NGNA present in the covalently-bound sialic acid residues on the native or recombinant glycoproteins may be reduced by manipulating the culture environment in such a way as to increase the dissolved carbon dioxide and/or carbonate species.

In a preferred embodiment the method of monitoring liquid phase $pCO_2$ is selected from: 1) sampling and analyzing media from the bioprocessing system; or 2) incorporating into the bioprocessing system a probe designed to measure liquid phase $pCO_2$.

In a preferred embodiment the method of adjusting dissolved carbon dioxide and/or carbonate species is selected from: 1) metering controlled mixtures of gasses the gas phase; 2) changing the exchange rate of gasses between the liquid and gas phases of the reactor; 3) changing the exchange rate of the immediate cell-culture gas phase with the gas in an external reservoir. The invention further comprises controlling carbon dioxide and/or carbonate species by increasing the amount of dissolved bicarbonate in the production media.

Additional elements that provide preferred embodiments of the invention include controlling one or more of the following cell culture and/or production parameters: 02; pH; lactate; and glucose. As would be understood by a person having knowledge of the art, the invention encompasses methods of controlling NGNA levels having various. combinations of these additional elements.

BRIEF DESCRIPTION OF THE DRAWINGS

FIG. 4 shows lactate profiles from runs 1.1–1.6 demonstrating the accumulation of acids during biosynthesis. Plotted are the measured daily lactate sample concentrations (higher of each pair) and the calculated lactate concentrations after dilution by make-up volume for each daily sample (lower of each pair) [g/L] versus the cumulative time of the experimental incubation. Daily changes in molar lactate content in each flask were calculated and an equimolar equivalent of 1N NaOH was added to titrate against the acidity.

These show pH profiles from twelve experimental T-flasks. Plotted are the measured daily pH levels (lower of each pair) and the calculated pH after titration with NaOH for each daily sample (higher of each pair) versus the cumulative time of the experimental incubation. Calculations are based upon known titration slopes ($\partial pH/\partial mM$ NaOH) for the experimental media.

DETAILED DESCRIPTION

The methods by which certain cell culture and/or production parameters are monitored and adjusted so as to control NGNA levels in a production process are described in more detail in the discussion below and are illustrated by the example provided below. The example shows various aspects of the invention and includes results of NGNA control by manipulation of environmental parameters. The results were surprising in that the relative and/or absolute amount of NGNA present in the covalently-bound sialic acid residues on the recombinant glycoproteins was reduced by increasing the level of liquid phase $pCO_2$.

In general, control of dissolved carbon dioxide and/or carbonate levels in the bioprocessing systems of the present invention involves controlling one or both of the following: 1) the exchange rate of carbon dioxide between the liquid and gas phases; or 2) the mean $pCO_2$ in the gas phase. In the present invention, the gas phase is defined as the overhead space of a stirred bioreactor, roller bottle, or T-flask; 2) the sparging gas of a stirred, airlift, or immobilized biomass bioreactor; 3) the gas phase of fibers in a hollow-fiber bioreactor; or 4) the gas phase of tubes in a stirred bioreactor fitted with gaspermeable tubing immersed in the liquid phase.

In the present invention, the methods of controlling the exchange rate of carbon dioxide between the liquid and gas phases include changing the agitation rate, sparging rate, surface to volume ratio, or permeability of a gas-exchange membrane.

Methods for controlling $pCO_2$ in the gas phase contemplated for use in the present invention include 1) metering controlled mixtures of gasses into the gas phase; or 2) changing the exchange rate of the immediate cell-culture gas phase with the gas in an external reservoir, such as the atmosphere in an incubator.

Also comprehended by the invention is the control of dissolved carbon dioxide and/or carbonate species by increasing the amount of dissolved bicarbonate.

Contemplated for use in the present invention are production processes for a variety of recombinant glycoproteins. Exemplary proteins are glycoproteins containing N-linked and/or O-linked oligosaccharides including EPO, and stem cell factor (SCF). Processes for producing these glycoproteins are known in the art (U.S. Pat. No. 4,703,008 to Lin, and WO 91/05795 to Zsebo et al. (1990), respectively.) Also contemplated are membrane-bound glycoproteins such as those which might be intrinsic to a vaccine or other therapeutic, as well as immunoglobulin containing N-linked and/or O-linked oligosaccharides.

In general, EPO useful in the present invention has the sequence of human erythropoietin, or closely related analogues thereof. The EPO may be produced by mammalian cells outside the body, or it may be isolated from natural sources. Preferably, the EPO is recombinant EPO (rEPO) produced as described in U.S. Pat. No. 4,703,008 to Lin, the disclosure of which is incorporated herein by reference. The preferred host cells are Chinese Hamster Ovary (CHO) cells as described in Example 10 of the Lin patent. Other host cells known in the art, e.g. baby hamster kidney cells, may also be used to produce EPO useful in the present invention. While the procedures of Example 10 in the Lin patent are the preferred method for producing rEPO, modifications and changes could be made to that process as known in the art.

Recombinant human erythropoietin contains three N-linked and one O-linked oligosaccharide chains which together comprise about 40% of the total molecular weight of the glycoprotein. The oligosaccharide chains have been shown to be modified with terminal sialic acid residues, including NGNA. To date, no human serum samples have tested positive for antibodies to EPO.

The type of bioprocessing system contemplated for use in the present invention include flat-bottomed, quiescent tissue culture flasks (T-flasks), roller bottles, stirred bioreactors for microcarrier or suspension cultures, fluidized beds, spinner flasks, and immobilized bed bioreactors including hollow-fiber bioreactors.

The methods of the present invention also contemplate the control of other cell culture and/or production parameters including pH, $pO_2$, lactate, and glucose.

Although the invention has been described and illustrated with respect to certain methods of monitoring and adjusting a cell culture and/or processing parameter in order to control NGNA levels, it will be apparent to one of ordinary skill that additional methods of controlling NGNA levels may exist without departing from the scope of the invention.

The following example will illustrate in more detail the various aspects of the present invention.

EXAMPLE a1

Controlled experiments using a modified T-flasks processing system were conducted to investigate the effects of various chemical and biochemical parameters on sialic acid composition in secreted recombinant EPO from CHO cells. CHO cells expressing EPO, as described in U.S. Pat. No. 4,703,008 to Lin, were used.

1. System used to evaluate effects of parameters

Figure 1:
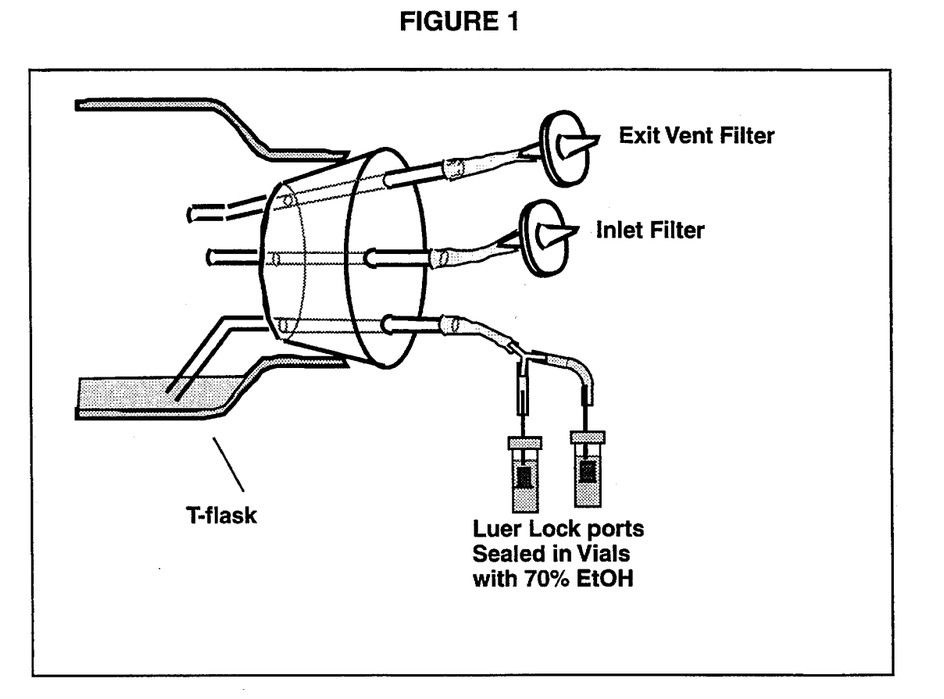
FIG. 1 is a schematic of the venting/sampling stopper system designed to replace the fitted-vented screw cap on the Falcon 3113 300 $cm^2$ T-flasks. This system was used to develop the experimental T-flasks used in the invention.

Initial work was performed to develop a T-flask system to use to control levels of $CO_2$. A modified system was needed to overcome the limitations (i.e., as they relate to controlling the experimental parameters) inherent in the use of vented-capped or closed-capped T-flask systems. A modified T-flask system was developed by replacing a single vented cap with a #9 stopper bored with three holes. Three stainless steel tubes penetrate the stopper. Two are connected on the exterior side to aseptic (0.2 μm) vent filters. The third tube is immersed in the media inside the flask and is connected to stainless steel luer-lock type sample ports. The latter are immersed in 70% ethanol to maintain sterility. One port is used to flush the other after sampling. The entire assembly can be autoclaved prior to attachment to the T-flask. FIG. 1 provides a schematic of the T-flask assembly.

Figure 2:
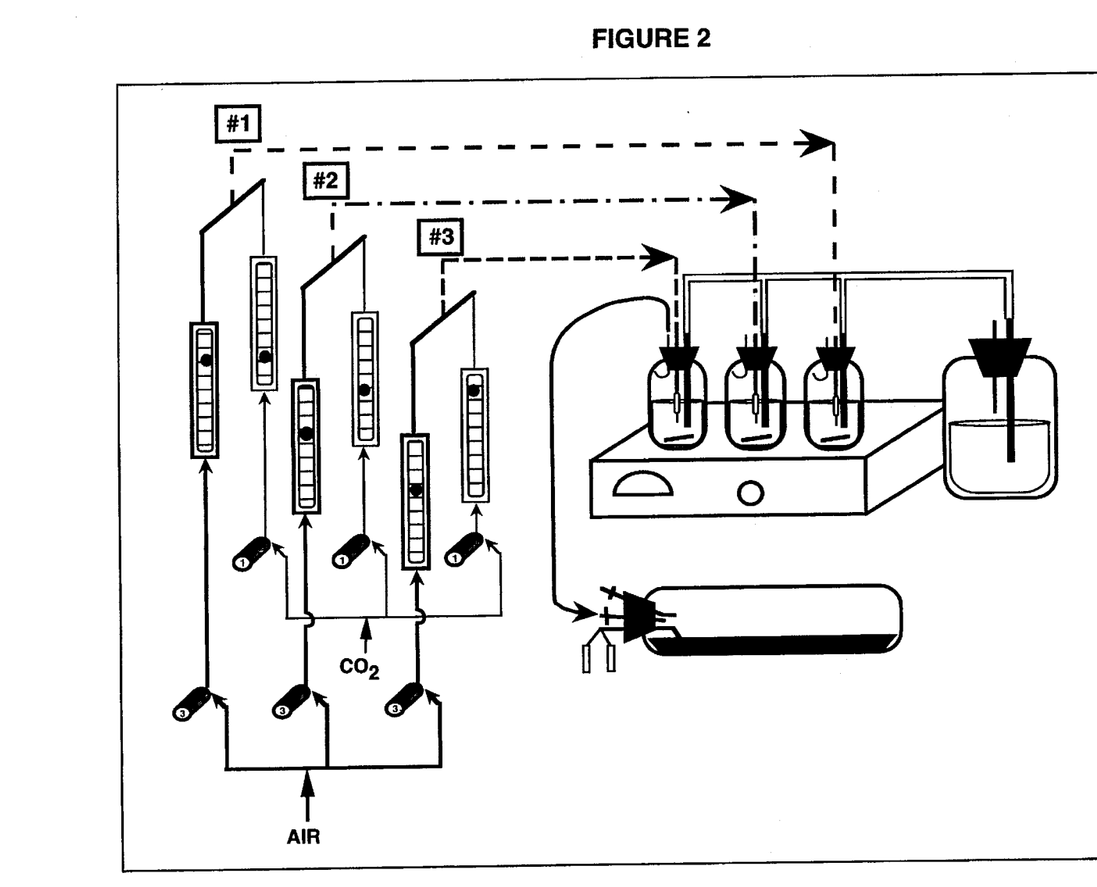
FIG. 2 is a schematic of the gassing and humidification assembly used to supply metered gas mixtures to the venting/sampling T-flask assembly detailed in FIG. 1. This assembly was used to investigate effects of environmental parameters on NGNA composition.

A gassing and humidification assembly (see FIG. 2) is then used to supply metered gas mixtures to the vented T-flask assembly. In this assembly, air or carbon dioxide at 14 psig are manifolded to pairs of rotameters (Cole Parmer)(indicated as vertical rectangles with graduated faces). Needle control valves (Brooks 8500 series #1 or #3 needle valves) (indicated as cylinders with numbered faces) are situated upstream of the rotameters. These valves were used for the precise control of gas flow through the pairs of rotameters. The gas streams from the paired rotameters are mixed and sparged through water in enclosed vessels. The vessels are fitted with magnetic stir bars which are agitated over a stir plate to enhance gas-liquid mass transfer. The gas exiting the humidification vessels is sent directly to the T-flask inlet vent filter as indicated in FIG. 2.

2. Preparation of suspension cultures

CHO cells transfected with a DNA sequence encoding human EPO, as described in U.S. Pat. No. 4,703,008 to Lin, were passaged continuously in suspension culture with growth media. Growth media consisted of DMEM/F-12 (Dulbecco's Modified Eagles Medium/Ham's F-12 50%/50% composition mixture, Gibco) buffered with 2.4 g/L sodium bicarbonate, and supplemented with 5% Fetal Bovine Serum and 100 nM methotrexate. Cultures were maintained in 1L spinner vessels, gassed initially with air containing 10 mole % $CO_2$, and incubated at 37° C. Cells were inoculated at between 1 and $2\times10^5$ cells/mL, grown to 0.5 to $1\times10^6$ cells/mL, and split by dilution as necessary.

3. Media preparation

The treatment media was comprised of DMEM/F-12 buffered initially with 15 mM HEPES (Sigma) and supplemented with 1X penicillin/streptomycin (Sigma) and 1X L-glutamine (Gibco). These basal media were then adjusted to desired initial conditions of pH and $pCO_2$ by adding sodium bicarbonate, and then adjusting pH and $pCO_2$ using 1N HCl and/or 1N NaOH, alternating with sparging using $CO_2$ and/or compressed air. The pH and $pCO_2$ were measured using a blood-gas analyzer (Corning Model 178 pH/Blood Gas Analyzer). Finally, osmolarity was measured and adjusted to the desired range (300 to 350 mMolal) by adding NaCl or diluting slightly with purified water. Osmolarity was measured using a vapor pressure osmometer (Wescor). Table 1 describes medium formulation and initial conditions for a range of conditions as described therein.

TABLE 1

| Sample I.D. | Adjustments per Liter | | | | Final Conditions | | |
|---|---|---|---|---|---|---|---|
| | NaHCO$_3$ g | 1N HCl mL | 1N NaOH mL | NaCl g | pCO$_2$ mm Hg | pH | Osm mMolal |
| 1.1 | 0.32 | — | 0.6 | — | 10 | 6.70 | 307 |
| 1.2 | 0.32 | — | 4.8 | — | 5 | 7.13 | 305 |
| 1.3 | 2.40 | 13.2 | — | — | 69 | 6.78 | 341 |
| 1.4 | 2.40 | — | 0.2 | — | 75 | 7.10 | 339 |
| 1.5 | 2.40 | 4.0 | — | — | 153 | 6.76 | 316 |
| 1.6 | 3.88 | — | 14.0 | — | 160 | 7.10 | 341 |
| 2.1 | 0.64 | — | 2.0 | — | 20 | 6.70 | 319 |
| 2.2 | 1.28 | 2.2 | — | 0.6 | 20 | 7.11 | 324 |
| 2.3 | 1.28 | 7.0 | — | 0.6 | 40 | 6.71 | 329 |
| 2.4 | 2.53 | 9.4 | — | — | 38 | 7.16 | 325 |
| 2.5 | 1.90 | 2.8 | — | 0.3 | 120 | 6.74 | 334 |
| 2.6 | 3.79 | — | — | — | 119 | 7.12 | 348 |

4. Inoculation of flasks

To perform the experiments, suspension cultures as prepared above were inoculated into T-flasks at $10^7$ cells per flask with a total of 200 mL of fresh growth medium per flask. Flasks were Becton-Dickenson Falcon® brand T-flask (Part Number 3113) with a 1.9 L volumetric capacity, 300 cm$^2$ surface area, and a 4 cm diameter mouth, and a vented cap. Cultures were incubated at 37° C. in a 5% or 10% CO$_2$ atmosphere for 4 to 6 days, at which time cell densities approached 1 to 2 x $10^8$ cells per T-flask. After the growth period, cultures were washed 2X with Dulbecco's Phosphate Buffered Saline (D-PBS) (50 mL) to remove serum, and 150 to 200 mL of the treatment media as described in Table 1 was added.

5. Gassing and venting of the experimental flasks

After feeding the T-flasks with the media, the vented flask caps were replaced with the customized stoppers described in Example 1. The flasks were then transferred to a 37° C. incubator where one of the vent lines from each flask was connected to the gassing and humidification assembly described in Example 1. Gas was supplied from high pressure sources (compressed CO$_2$ or compressed air), regulated to 14 psig, and manifolded to the pairs of reducing valves. Pressure-reduced, compressed air was controlled through rotameters calibrated for a maximum flow rate of 90 standard mL air/minute. Generally, the flow was adjusted in the range from 60 to 100% of the maximum, according to the balance required to achieve the desired pCO$_2$. Carbon dioxide was controlled through rotameters calibrated for a maximum flow rate of 12 standard mL air per minute. Carbon dioxide flow was adjusted in the range from 15 to 100% of the maximum, according to the desired pCO$_2$ level. Air and carbon dioxide streams from paired rotameters were joined and sparged through a stirred humidification chamber containing water at 37° C. Humidified gas was then manifolded to pairs of T-flasks. Gas compositions were checked at the exit vent filters from each T-flask using a blood gas analyzer (Corning Model 178 pH/Blood Gas Analyzer), and adjustments to the rotameter flows were made accordingly.

6. Sampling of the flasks for analysis

T-flasks were sampled daily (8 to 10 days) for off-gas composition, and for levels of pH, pCO$_2$, pO$_2$, glucose, and lactate. Because the stopper apparatus was not easily removed and replaced during sampling, media samples were withdrawn via luer lock ports connected to a siphon tube immersed in the media. Generally, a 3–5 mL void sample was withdrawn and discarded, then a 5–10 mL sample was withdrawn for analysis. Make-up media was introduced via a sterile filter (0.45 μm cut-off) to replenish volume lost through sampling. Also, the pH was adjusted by addition of 1N NaOH to titrate against the accumulation of lactate (see FIG. 4). This method was found to maintain the pH near the original media set point. Finally, the sample port was then flushed with 70% ethanol and stored in a 70% ethanol bath to retain sterility. After immediate metabolic analysis, samples were saved at −20° C. for subsequent determination of EPO titers. The EPO titers (as measured by ELISA) varied from 1500 to 2400 U/ml for the twelve conditions.

7. Parameter profiles a. glucose, lactate and pO$_2$ profiles

Figure 3:
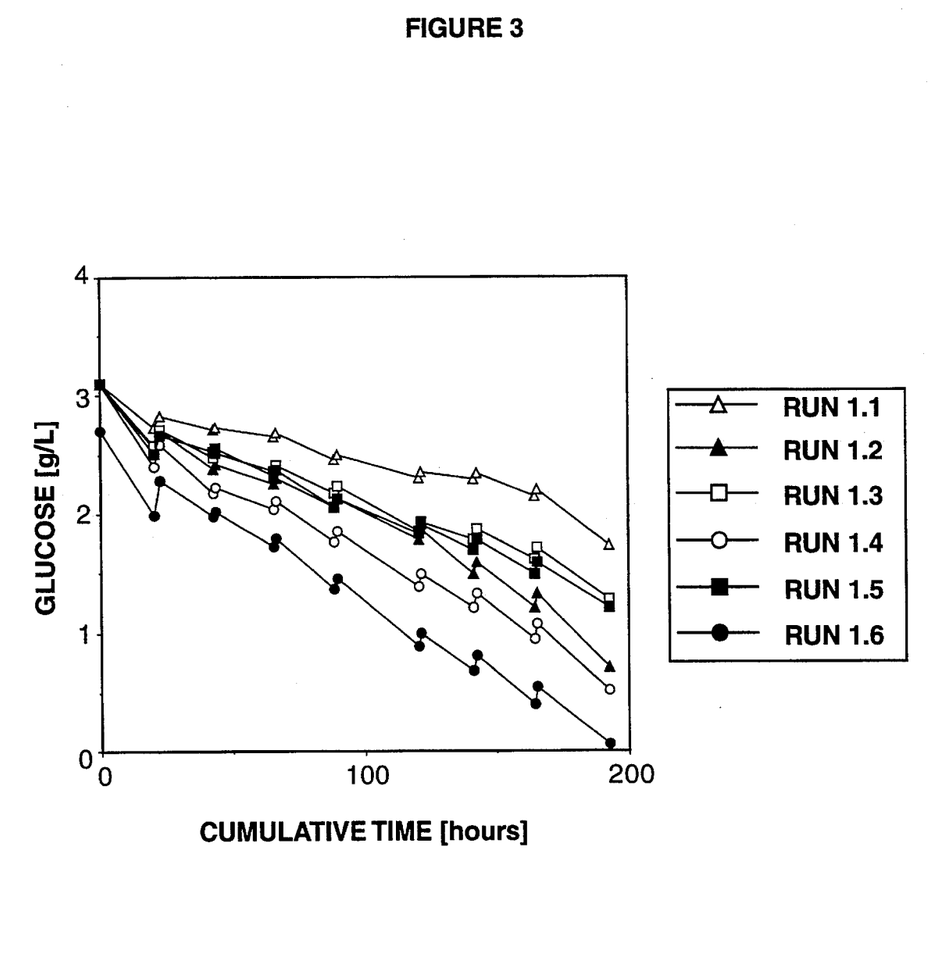
FIG. 3 shows glucose profiles from runs 1.1–1.6 demonstrating that glucose metabolism was sustained throughout biosynthesis. Plotted are the measured daily glucose sample concentrations (lower of each pair) and the calculated glucose concentrations after makeup addition for each daily sample (higher of each pair) [g/L] versus the cumulative time of the experimental incubation. Runs 1.1–1.5 contained 3.1 g/L glucose initially. Run 1.6 contained 2.7 g/L glucose because the media was diluted slightly to maintain osmolarity below 350 mmolal.
Figure 4:
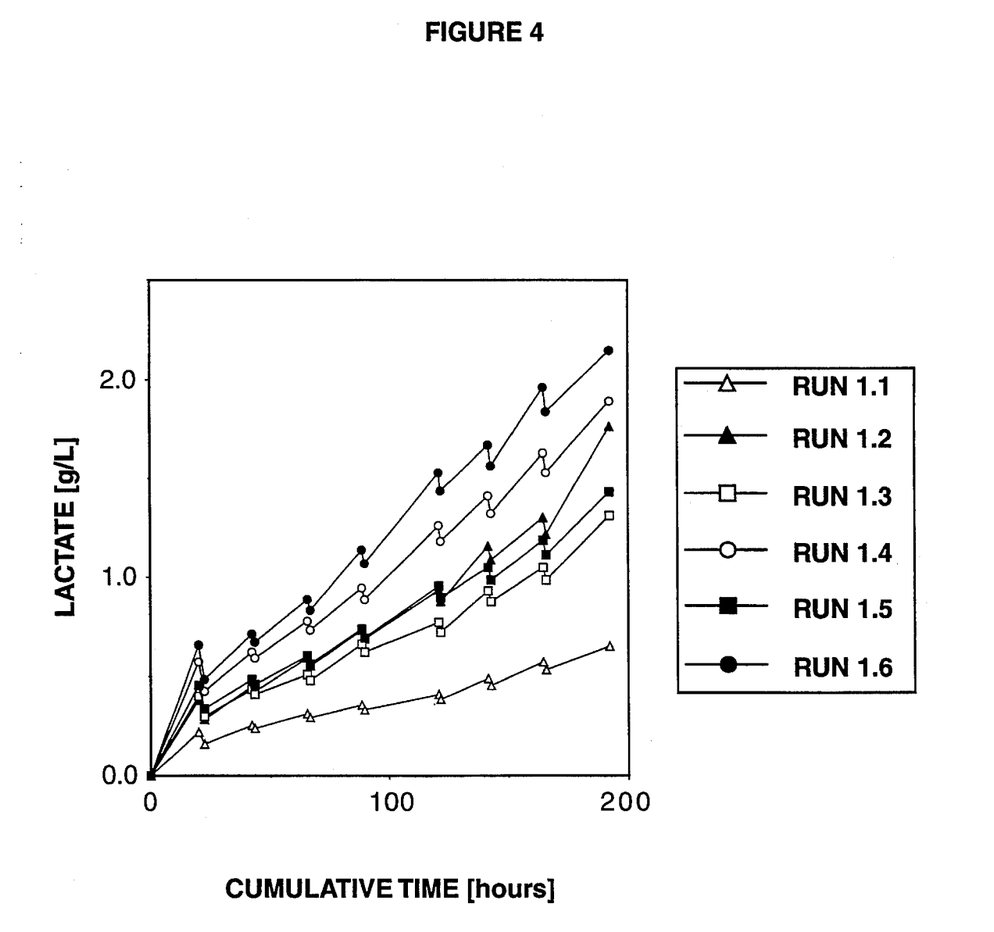
Figure 5:
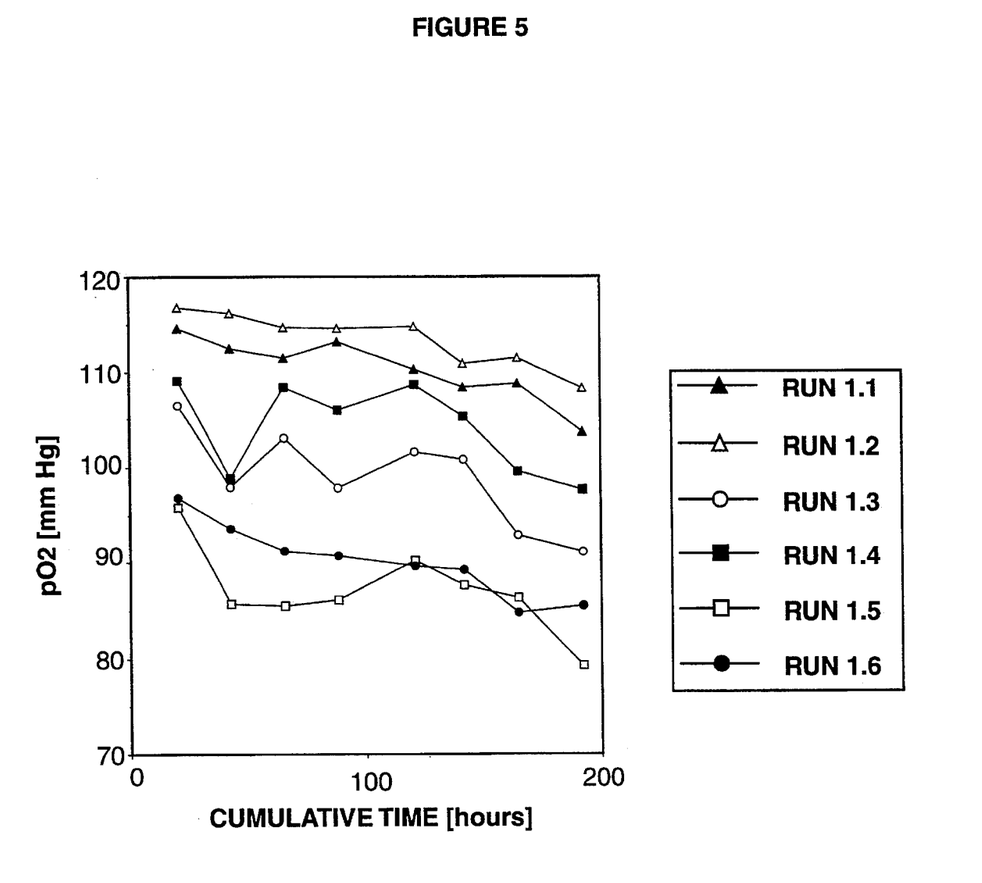
FIG. 5 shows dissolved oxygen profiles from six experimental T-flasks. Plotted are the measured daily $pO_2$ levels [mm Hg] versus the cumulative time of the experimental incubation.

FIGS. 3, 4, and 5 show the glucose, lactate, and pO$_2$ profiles, respectively, from the first 6 conditions (1.1–1.6 in Table 1). Since these variables were essentially uncontrolled, and since their range of variation is unlikely to demonstrate an effect on NGNA composition, the comparable data from the other 6 conditions are not shown.

FIGS. 3 and 4 show the glucose and lactate profiles for runs 1.1–1.6. Glucose and lactate concentration was analyzed using a YSI 2700 Select Biochemistry Analyzer. Glucose and lactate are monitored for purposes of gauging metabolic activity and controlling pH. Although the profiles vary systematically between the runs, there is no functional relationship between metabolic rate and NGNA.

FIG. 5 shows the pO2 profile for runs 1.114 1.6. The flasks were analyzed for dissolved oxygen concentration using a Corning Model 178 pH/Blood Gas Analyzer. The data show that pO$_2$ was maintained within a range sufficient to support metabolic activity. Independent studies have shown no effect of gas-phase pO$_2$ on EPO NGNA content.

b. pCO$_2$ and pH profiles

Figure 6:
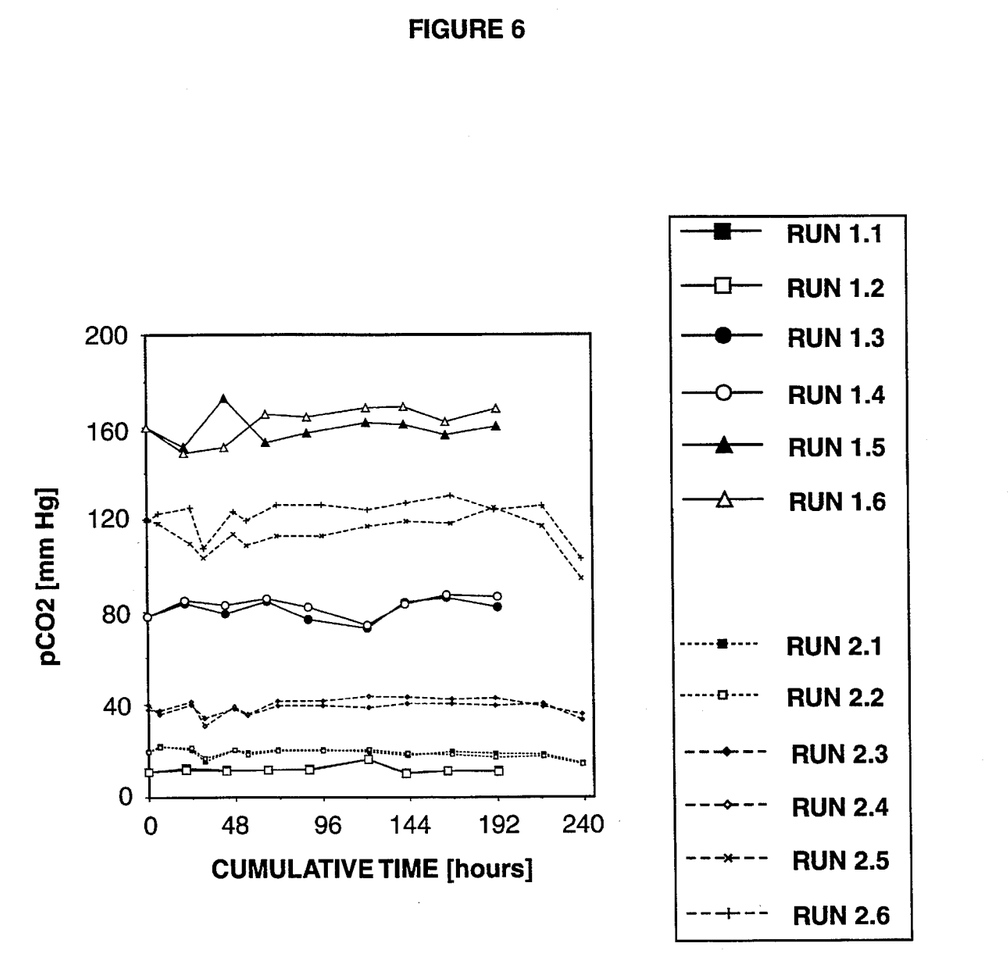
FIG. 6 shows dissolved carbon dioxide profiles from twelve experimental T-flasks. Plotted are the measured daily $pCO_2$ levels [nun Hg] versus the cumulative time of the experimental incubations.
Figure 7A:
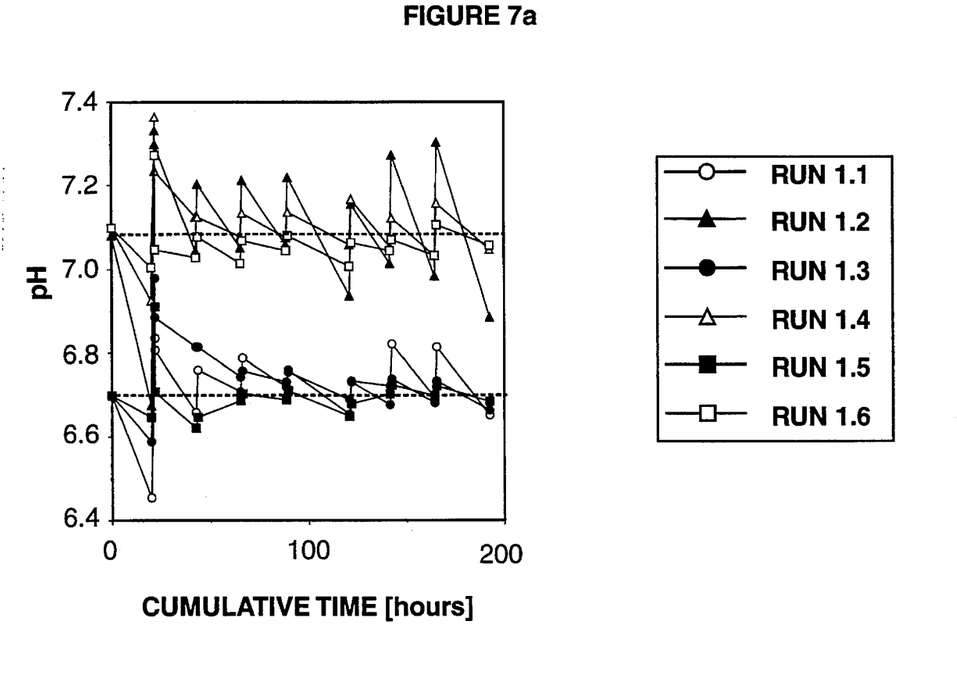
FIG. 7a shows results for first experiment and FIG. 7b for the second experiment.
Figure 7B:
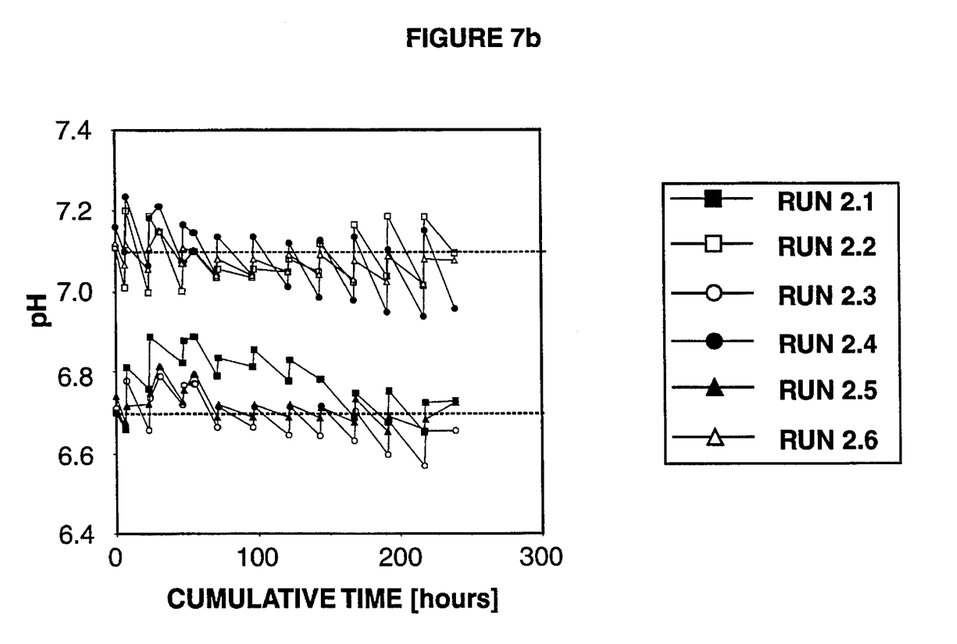

The pCO$_2$ and pH profiles for runs 1.1–1.6 and 2.1–2.6 are shown in FIGS. 6, 7a and 7b, respectively. The experiments were designed to control pCO$_2$ at or near six statistically distinct levels. Samples were analyzed for liquid phase pCO$_2$ and pH using a Corning Model 178 pH/Blood Gas Analyzer. The liquid phase pCO$_2$ was controlled within acceptable tolerances throughout the experimental runs. pH was also purposefully controlled at two statistically distinct levels. A paired t-test from each of the sets of runs with similar pCO$_2$ levels shows no significant effect of pH on NGNA composition for these experiments (see FIG. 8).

8. Harvesting of media for analysis

After sufficient EPO was accumulated in the flasks for determination of sialic acid composition (generally $4 \times 10^5$ units), the media was harvested, filtered, and stored at −20° C. Several flasks were trypsinized and counted to determine final cell density.

9. Analytical method for determining NGNA composition

Cell culture conditioned media containing glycosylated EPO was concentrated approximately 3–5 fold using a Centriprep-10 (Amicon, cat. #4304). This concentrate was then partially purified by anion exchange chromatography. A 600uL bed volume of DEAE Bio-Gel Agarose (Bio-Rad, cat. #153–0740) was poured into a poly-prep chromatogjraphy column (Bio-Rad, cat. #731–1550). The resin was equilibrated with four column volumes of 10 mM TRIS, pH 7.0. The concentrated conditioned media was diluted 1:10 with $dH_2O$ (i.e. 2mL of media/18mL $dH_2O$) so that the conductivity would be equal to or less than that of the 10mM TRIS buffer. This diluted material was added to the resin and the unbound fraction (flow through) was collected. After loading, the column was washed with four column volumes of the TRIS buffer, this wash was combined with the flow through. The adsorbed EPO was eluted from the column with 10mM TRIS+75 mM NaCl+20uM $CuSO_4$, pH 7.0

This eluted material was then subjected to concentration and diafiltration into $dH_2O$. Approximately 1800uL of the eluted EPO solution was concentrated ~10 fold in a Centricon-10 (Amicon, cat. # 4205) using a Beckman J6B centrifuge at 5000 rpm. Subsequently, the sample was buffer exchanged into $dH_2O$ by adding 1000uL of $dH_2O$ to the centricon and centrifuging as before for ~90 minutes. The EPO concentration of this final diafiltered material is determined by ELISA.

The sialic acid groups attached to the EPO molecule were then released by digestion with Neuraminidase Arthrobacter ureafaciens (Calbiochem, cat. # 480714) The EPO sample was adjusted to a final protein concentration of 0.25 mg/mL. Approximately 0.1 Units of Neuraminidase will digest 0.25 mg of EPO. Hence, 10uL of the 10 Units/mL stock Neuraminidase solution was added to the EPO sample. Also, sodium azide was added to this solution to a final concentration of 5mM by dilution with a 1M sodium azide solution. This solution was mixed and then incubated at 37° C overnight (18 hours) to digest. The digested samples were centrifuged in Centricon-10's at 5000 rpm for 45 minutes. The filtrate, containing the lower molecular weight sialic acids, was subjected to carbohydrate analysis on a Dionex HPAE-PAD system (Dionex Corp., Sunnyvale CA). A usual analytical run contains ~50 ug of protein sample in 200uL. Molar compositions of the sialic acids were estimated from the relative Dionex peak areas of the NGNA and NANA species, adjusting for relative detector response to each species as determined from a standard curve prepared from mixtures of known molar composition.

10. Summary of the experimental parameters and resulting NGNA composition

Mean and standard deviations for $pCO_2$ and pH over the incubation periods, together with the estimated molar compositions of sialic acid (mole percent NGNA) are summarized in Table 2.

TABLE 2

| SAMPLE I.D. | $pCO_2$ (mm Hg) | pH | % NGNA |
| --- | --- | --- | --- |
| 1.1 | 12.4 ± 1.8 | 6.73 ± 0.06 | 4.21 ± 0.38 |
| 1.2 | 12.1 ± 2.0 | 7.10 ± 0.13 | 3.63 ± 0.33 |
| 1.3 | 81 ± 5 | 6.73 ± 0.05 | 2.31 ± 0.21 |
| 1.4 | 83 ± 4 | 7.10 ± 0.04 | 2.05 ± 0.18 |
| 1.5 | 160 ± 6 | 6.69 ± 0.03 | 1.47 ± 0.13 |
| 1.6 | 164 ± 6 | 7.05 ± 0.03 | 1.79 ± 0.16 |
| 2.1 | 19.2 ± 2.1 | 6.78 ± 0.09 | 3.84 ± 0.34 |
| 2.2 | 19.1 ± 2.1 | 7.08 ± 0.06 | 3.46 ± 0.31 |
| 2.3 | 38.1 ± 2.5 | 6.69 ± 0.06 | 3.06 ± 0.28 |

TABLE 2-continued

| SAMPLE I.D. | $pCO_2$ (mm Hg) | pH | % NGNA |
| --- | --- | --- | --- |
| 2.4 | 39.7 ± 3.7 | 7.09 ± 0.08 | 2.95 ± 0.26 |
| 2.5 | 113.2 ± 7.8 | 6.71 ± 0.04 | 1.67 ± 0.15 |
| 2.6 | 121.9 ± 7.8 | 7.08 ± 0.03 | 2.16 ± 0.19 |

Figure 8:
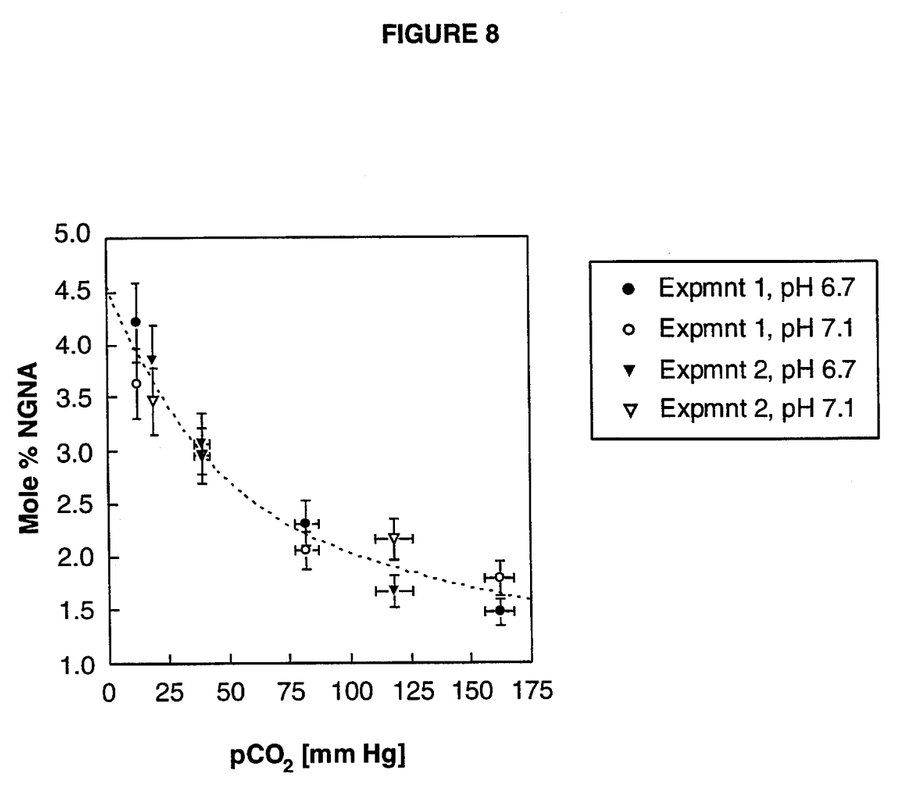
FIG. 8 shows a plot of the molar sialic acid composition versus carbon dioxide level. Plotted are the final mole percent NGNA versus the time-averaged $pCO_2$ levels for each of the twelve runs.

The functional relationship between $pCO_2$ and NGNA is shown in FIG. 8. The time-averaged $pCO_2$ levels and standard deviations in $pCO_2$ were computed from daily samples for each of the twelve runs (see FIG. 6). Standard deviations in NGNA content are estimated using a historical measurement of the assay precision (9% coefficient of variation). Although the data are consistent with a single functional relationship, points from independent experiments and pH treatments are resolved as indicated in the figure legend. FIG. 8 also demonstrates that the pH deviations observed in FIGS. 7a and 7b had no significant effect on NGNA composition.

This data shows that liquid-phase $pCO_2$ levels have a profound effect on the molar sialic acid composition of recombinant EPO produced in CHO cell culture. In two independent experiments comprising twelve independent runs, the mole percent NGNA was shown to be controlled in the range from 4.0% down to 1.6% by adjusting the levels of carbon dioxide in the range from 12 mm Hg to 162 mm Hg. A quadratic regression of the data indicates that 94% of the observed variation is explained by the effect of carbon dioxide. The change in NGNA composition is most pronounced at low $pCO_2$ values. The incremental effect of additional $pCO_2$ on NGNA composition decreases with increasing $pCO_2$.

The ranges of $pCO_2$ investigated are typical of those found in many large-scale bioprocessing systems. It is not technically difficult to achieve significant increases in dissolved $pCO_2$ within these ranges. For $pCO_2$ levels above 120 mm Hg at neutral pH the additional osmolarity contributed by bicarbonate anion can be significant (>32 mmolal excess relative to media in equilibrium with 10% $CO_2$), but this can be compensated by reducing the sodium chloride levels in the basal media. Therefore, the results presented herein demonstrate a practical method for controlling the sialic acid composition of secreted recombinant glycoproteins which should apply to a variety of bioprocessing systems.

What is claimed is:

1. In a process for producing a glycopretin in a reaction mixture, a method for controlling levels of N-glycolylneuraminic acid (NGNA) in said glycoprotein, the method comprising:

monitoring levsls of $CO_2$ in the reaction mixture during biosynthesis of said glycoprotein; and adjusting levels of $CO_2$ in the reaction mixture during biosynthesis of said glycoprotein.

2. The method of claim 1 wherein said $CO_2$ is present in the reaction mixture in the form of dissolved carbon dioxide species, carbonate species, or mixtures of both.

3. The method of claim 2 wherein the reaction mixture comprises a liquid and gas phase and said adjustment of $CO_2$ levels comprises controlling the exchange rate of carbon dioxide between the liquid and gas phases.

4. The method of claim 3 wherein control of said exchange rate of carbon dioxide between the liquid and gas phases is effected by changing the agitation rate, changing the sparging rate, changing the surface to volume ratio, or changing the permeability of a gas-exchange membrane.

5. The method of claim 2 wherein the reaction mixture comprises a liquid and gas phase and said adjustment of $CO_2$ levels comprises controlling the $pCO_2$ in the gas phase.

6. The method of claim 5 wherein control of pCO2 in the gas phase comprises metering controlled mixtures of gasses into the gas phase.

7. The method of claim 5 wherien control of $pCO_2$ in the gas phase comprises changing the exchange rate of the immediate cell-culture gas phase with the gas in an external reservoir.

8. The method of claim 2 wherein the adjustment of $CO_2$ levels comprises increasing the amount of dissolved bicarbonate in the reaction mixture.

9. The method of claim 1 wherein said process of production is carried out in one of the following biosynthesis systems: tissue culture flasks, roller bottles, stirred bioreactors for microcarrier or suspension cultures, hollow-fiber bioreactors, fluidized beds, spinner flasks, or immobilized bed bioreactors.

10. The method of claim 1 wherein said glycoprotein contains N-linked and/or O-linked oligosaccharides.

11. The method of claim 10 wherein said glycoprotein is selected from the group consisting of EPO, stem cell factor, and granulocyte colony stimulating factor, immunoglobulin, and membrane-bound glycoprotein intrinsic to a vaccine or other therapeutic.

12. In a process for producing a glycoprotien in a reaction mixture, a method for lowering levels of N-glycolyl-neuraminic acid (NGNA) in said glycoprotein, the method comprising increasing levels of $CO_2$ in the reaction mixture during biosynthesis of said glycoprotein.

13. The method of claim 12 wherein said $CO_2$ is present in the reaction mixture in the form of dissolved carbon dioxide species, carbonate species, or mixtures of both.

14. The method of claim 13 wherein the reaction mixture comprises a liquid and gas phase and said adjustment of $CO_2$ levels comprises controlling the exchange rate of carbon dioxide between the liquid and gas phases.

15. The method of claim 14 wherein control of said exchange rate of carbon dioxide between the liquid and gas phases is effected by changing the agitation rate, changing the sparging rate, changing the surface to volume ratio, or changing the permeability of a gas-exchange membrane.

16. The method of claim 13 wherein the reaction mixture comprises a liquid and gas phase and said adjustment of $CO_2$ levels comprises controlling the $pCO_2$ in the gas phase.

17. The method of claim 16 wherein control of pCO2 in the gas phase comprises metering controlled mixtures of gasses into the gas phase.

18. The method of claim 16 wherein control of $pCO_2$ in the gas phase comprises changing the exchange rate of the immediate cell-culture gas phase with the gas in an external reservoir.

19. The method of claim 13 wherein the adjustment of $CO_2$ levels comprises increasing the amount of dissolved bicarbonate in the reaction mixture.

20. The method of claim 12 wherein said process of production is carried out in one of the following biosynthesis systems: tissue culture flasks, roller bottles, stirred bioreactors for microcarrier or suspension cultures, hollow-fiber bioreactors, fluidized beds, spinner flasks, or immobilized bed bioreactors.

21. The method of claim 12 wherein said glycoprotein contains N-linked and/or O-linked oligosaccharides.

22. The method of claim 21 wherein said glycoprotein is selected from the group consisting of EPO, stem cell factor, and granulocyte colony stimulating factor, immunoglobulin, and membrane-bound glycoprotein intrinsic to a vaccine or other therapeutic.

* * * * *

UNITED STATES PATENT AND TRADEMARK OFFICE
CERTIFICATE OF CORRECTION

PATENT NO.   : 5,459,031
DATED        : October 17, 1995
INVENTOR(S)  : Tracy K. Blumen; Gustavo E. Grampp; David J. Hettwer It is certified that error appears in the above-identified patent and that said Letters Patent is hereby corrected as shown below:

Column 3, line 5, "4:366-373 (1993)" should be --9:366-373 (1993)--.

Column 3, line 41, after "gasses" insert --into--.

Column 3, line 51, "O2" should be --$O_2$--.

Column 3, line 54, "various." should be --various--.

Column 4, line 67, "gaspermeable" should be --gas permeable--.

Column 8, line 44, "1.1141.6" should be --1.1-1.6--.

Column 10, line 48, in claim 1, "glycopretin" should be --glycoprotein--.

Column 10, line 53, in claim 1, "levsls" should be --levels--.

Signed and Sealed this

Ninth Day of April, 1996

Attest:

BRUCE LEHMAN

Attesting Officer

Commissioner of Patents and Trademarks